(12) United States Patent
MacKugler

(10) Patent No.: US 11,058,066 B2
(45) Date of Patent: Jul. 13, 2021

(54) CUSTOMIZABLE PLANT GROWING SYSTEM

(71) Applicant: CloudFarm Inc., Middlebury, VT (US)

(72) Inventor: Cameron MacKugler, Middlebury, VT (US)

(*) Notice: Subject to any disclaimer, the term of this patent is extended or adjusted under 35 U.S.C. 154(b) by 478 days.

(21) Appl. No.: 15/507,352

(22) PCT Filed: Sep. 3, 2015

(86) PCT No.: PCT/US2015/048436
§ 371 (c)(1),
(2) Date: Feb. 28, 2017

(87) PCT Pub. No.: WO2016/037011
PCT Pub. Date: Mar. 10, 2016

(65) Prior Publication Data
US 2017/0280633 A1 Oct. 5, 2017

Related U.S. Application Data

(60) Provisional application No. 62/046,362, filed on Sep. 5, 2014.

(51) Int. Cl.
*A01C 1/04* (2006.01)
*A01G 9/029* (2018.01)
(Continued)

(52) U.S. Cl.
CPC ............... *A01G 9/029* (2018.02); *A01C 1/04* (2013.01); *A01C 1/042* (2013.01); *A01C 1/044* (2013.01);
(Continued)

(58) Field of Classification Search
CPC .......... A01C 1/04; A01C 1/042; A01C 1/044; A01C 1/046; A01C 1/06
(Continued)

(56) References Cited

U.S. PATENT DOCUMENTS 3,080,681 A * 3/1963 Merrill .................. A01G 20/00
47/56
3,673,134 A 6/1972 Anderson
(Continued)

OTHER PUBLICATIONS

U.S. Appl. No. 12/396,058, filed Sep. 2009, Kuschak.

*Primary Examiner* — David J Parsley

(57) ABSTRACT

The system includes a pre-fabricated garden seedsheet, with seeds and soil embedded in water-soluble pods within a weed barrier fabric. Each water-soluble pod is fabricated from dissolvable material, which are affixed together to form cavities in which seeds and soil are applied. The pods are then affixed to the weed barrier matrix in an arrangement dictated by the plant algorithm. Upon contact with water, the pods rapidly dissolve, thereby beginning the germination process in which the seeds sprout and emerge through the aligned openings in the weed barrier fabric. The selection of plants and their physical arrangement within each seedsheet may be determined by a software-driven plant algorithm that extrapolates plant characteristics, environmental requirements, and companion benefits. The algorithm may be used both on the customer-facing software program, as well as the in-house design process to create pre-designed seed sheets.

12 Claims, 4 Drawing Sheets

(51) Int. Cl.
*A01G 9/02* (2018.01)
*A01N 25/34* (2006.01)
*C12N 5/04* (2006.01)
A01G 9/00 (2018.01)
A01N 25/00 (2006.01)
C12N 5/00 (2006.01)

(52) U.S. Cl.
CPC .............. *A01G 9/02* (2013.01); *A01N 25/34* (2013.01); *C12N 5/04* (2013.01); A01G 9/00 (2013.01); A01N 25/00 (2013.01); C12N 5/00 (2013.01)

(58) Field of Classification Search
USPC .................................... 47/56, 57.6, 58.1 R
See application file for complete search history.

(56) References Cited

U.S. PATENT DOCUMENTS

| | | | | |
|---|---|---|---|---|
| 3,890,739 A | * | 6/1975 | Blackburn | A01G 20/20 47/56 |
| 3,914,900 A | | 10/1975 | Bigelow | |
| 4,190,981 A | * | 3/1980 | Muldner | A01G 20/20 47/56 |
| 4,911,304 A | * | 3/1990 | Bunin | B65D 75/327 206/531 |
| 5,205,068 A | * | 4/1993 | Solomou | A01G 20/20 47/56 |
| 5,401,281 A | * | 3/1995 | Chamoulaud | A01G 31/00 47/58.1 R |
| 5,417,010 A | * | 5/1995 | Ecer | A01C 1/044 47/56 |
| 5,490,351 A | * | 2/1996 | Molnar | A01G 20/20 47/56 |
| 6,389,745 B1 | * | 5/2002 | Huh | A01C 1/044 47/1.01 F |
| 6,681,521 B1 | | 1/2004 | Holloway | |
| 7,963,068 B2 | | 6/2011 | Cope | |
| 9,220,190 B2 | * | 12/2015 | Kennedy | A01C 1/044 |
| 9,521,803 B2 | * | 12/2016 | Ray, III | B31D 1/02 |
| 2006/0191194 A1 | | 8/2006 | Abitz | |
| 2007/0144065 A1 | | 6/2007 | Lowe | |
| 2008/0072488 A1 | | 3/2008 | Fujita | |
| 2009/0178334 A1 | | 7/2009 | Henderson | |
| 2009/0216661 A1 | | 8/2009 | Warner | |
| 2011/0152100 A1 | | 6/2011 | Parrish | |
| 2013/0112122 A1 | | 5/2013 | Bloome | |
| 2015/0257330 A1 | * | 9/2015 | Remme | A01C 1/042 47/56 |
| 2016/0174457 A1 | * | 6/2016 | Lynch | G06F 16/9554 47/56 |

* cited by examiner

CUSTOMIZABLE PLANT GROWING SYSTEM

CROSS-REFERENCE TO RELATED APPLICATION

This application claims priority to U.S. Provisional Application #62046362, filed Sep. 5, 2014; and to PCT application PCT/US2015/048436, filed Sep. 3, 2015

FEDERALLY-SPONSORED RESEARCH

None

BACKGROUND

The common practice of preparing a garden bed, buying bulk packets of seeds, and measuring out each individual plant's spacing requirements is a tedious and time-intensive process. Planning and planting a garden is a knowledge and labor intensive process that requires a gardener to know the spacing requirements for each plant, soil pH requirements, nutrient requirements, sunlight requirements, water requirements, pest management, and companion benefits between plant varieties. It is a highly complex calculation that takes into account a large variety of variables. The gardener may end up with a multitude of extra seeds and must keep them in a controlled environment to prevent rot and spoiling. In addition, the planting process usually results in hours spent uncomfortably kneeling over a garden, measuring and digging individual holes and rows, fumbling with frustratingly tiny seeds, and then frequently weeding to ensure a non-competitive and nutrient-rich growing atmosphere.

The present system serves to provide innovative solutions to the process of designing a garden, the process of physically sowing fruit, vegetable, flower, and herb seeds, the process of weed control, and the process of identifying recipes congruent with harvestable produce. The system provides the user the ability to chose an existing seedsheet SKU, or design their own garden, preferably online, and purchase a corresponding seedsheet that includes all of the plant seeds that they wish to grow with their ideal spacing characteristics. This system serves to codify the variability of plant environmental requirements into an algorithm that thereby simplifies the designing of a garden, the sowing of seeds, the weeding maintenance of a garden, the economical burden of overbuying seeds, and the searching of recipes congruent with available harvested ingredients. The plant algorithm may be used to create seed sheets, including but not limited to pre-designed SKU's, as well as future pre-designed products.

Through virtual design and the simple process of planting a seedsheet, the investigative thought-process of identifying environmentally compatible plants, and labor of physically sowing seeds is reduced to a brief online session and near-instantaneous unfurling of the seedsheet atop the garden. Additionally, the burdensome task of regular weeding that's usually necessary for the planted seeds to germinate (as well as continue to develop, as weeds often out-compete garden plants for available nutrients), is eliminated, or greatly reduced with the present system. This system serves to remove and greatly reduce the necessity for weeding by incorporating a weed barrier landscape fabric, with water-soluble/dissolvable fabric openings in the location of the user-selected seeds. As the seeds germinate and develop the weed barrier prevents any weeds from growing, and significantly limits any weeding to only the openings where the desired plants are sowed.

BRIEF SUMMARY

The present system includes an optimally designed prefabricated garden with seeds and soil embedded in water-soluble pods within a weed barrier fabric. The physical arrangement of plants within each product may be determined by a plant algorithm that extrapolates plant characteristics, environmental requirements, and companion benefits to design the most successful harvests possible. Each water-soluble pod is fabricated with dissolvable material including but not limited to fabric and films, which are affixed together to form cavities in which seeds and soil are applied. The pods are then affixed to the weed barrier matrix in an arrangement dictated by the design algorithm. Upon watering, the pods rapidly dissolve, thereby beginning the germination process in which the seeds sprout and emerge through the aligned openings in the weed barrier fabric. The algorithm may be used both on the customer-facing software program, as well as the in-house design process to create pre-designed seed sheets.

The present system may also include a software-driven and designed seed sheet that allows a customizable arrangement of seeds such as vegetable, herb, and flowers, to be adhered between disks of water-soluble/dissolvable fabric within a larger medium of weed-barrier fabric. The software program provides the user the ability to select which varieties of plants they wish to grow, and using a proprietary plant algorithm arranges the plants by their corresponding spacing requirements and compatibility with various environmental variables.

DETAILED DESCRIPTION

Figure 1:
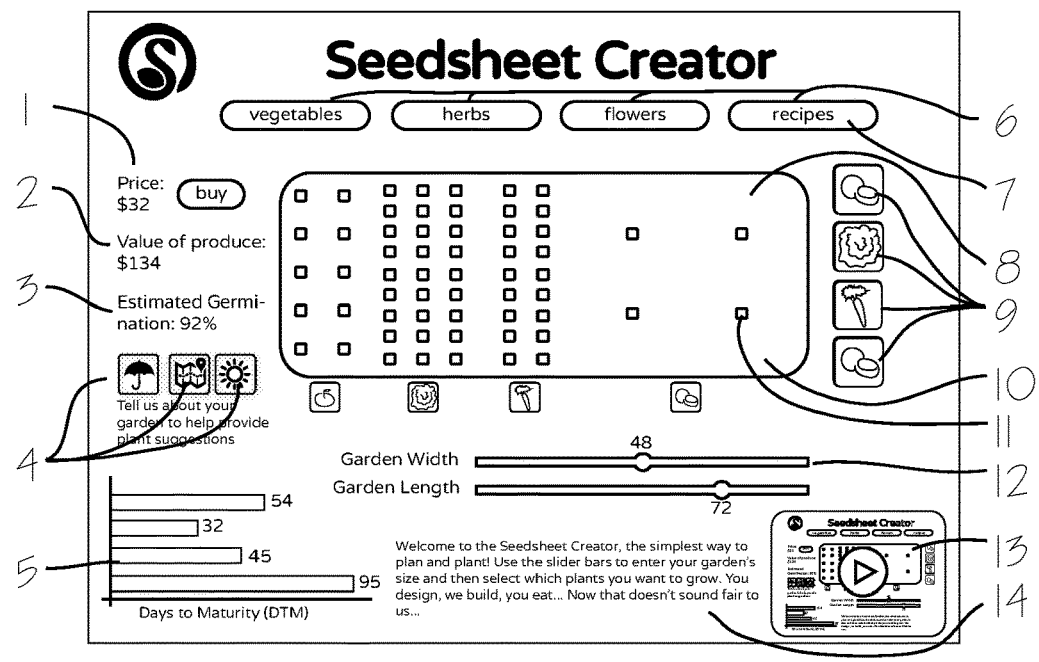
FIG. 1 shows interface for planning a garden and creating a seedsheet
Figure 2:
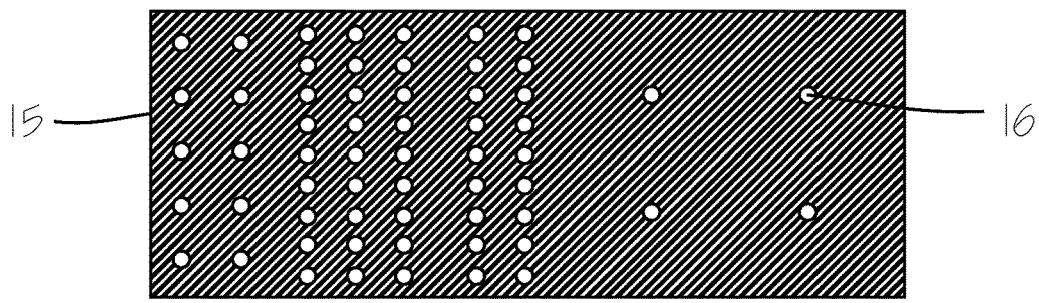
FIG. 2 shows the physical seedsheet created per the digital design
Figure 3:
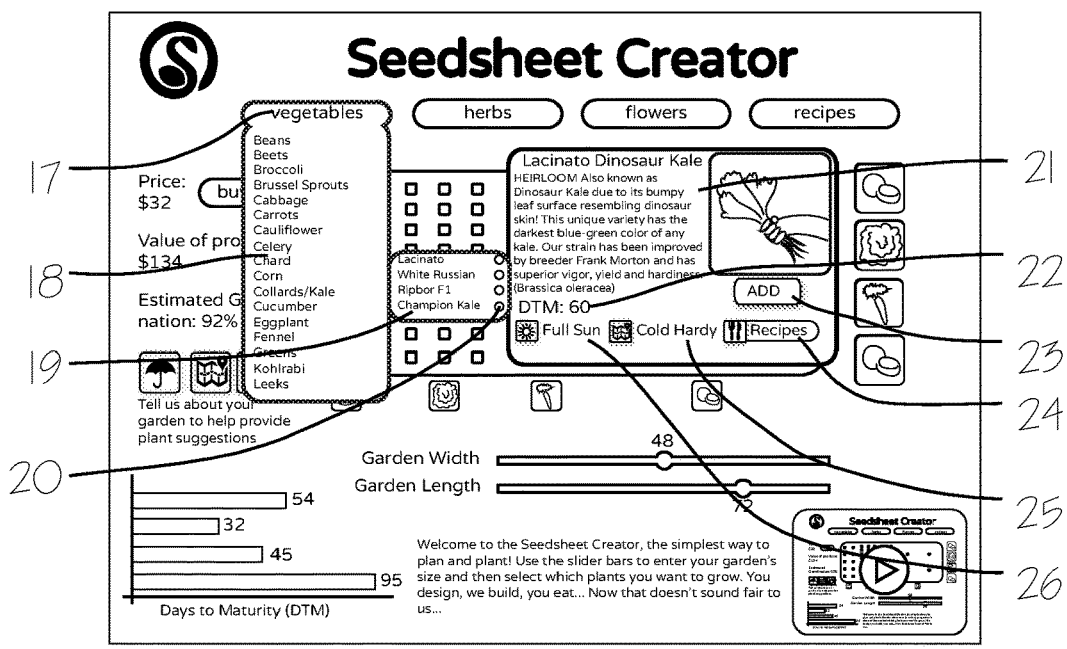
FIG. 3 shows additional features for an interface for planning a garden and creating a seedsheet

Described herein is a seedsheet system for selecting and growing plants. This system may optionally include the design of the seedsheet by a software program, for which a user interface is shown in FIG. 1. Such software may be in the form of a website, an app, or other suitable means for a user to interact with the interface. The software includes a gridded virtual garden (8) with a drag-drop interface to provide a digital plant arrangement (10) that corresponds to the layout of seeds (11), as shown in the virtual image of the seedsheet in FIG. 2.

The user begins by selecting the dimensions of their existing garden space (12), and next specifies the location (and subsequent garden climate according to appropriate guideline, such as but not limited to the USDA Plant Hardiness Map) of their garden (via zip code, or other location reference), as well as the sunlight availability of their garden (4). user then selects which vegetables, herbs, and flowers (17,18,19) they wish to plant based on the size, location, and sunlight availability of their garden, the software filters available plant selection by plants that will thrive in that specific environment (20). this selection process the user may see information (21) regarding the requirements of the plant, such as the sunlight requirement (26), climate requirement (25), days-to-maturity/DTM (22), and recipes from the Recipe Database that include that specific plant (24). When a specific plant is selected (23, 9), a colored block (10) is placed onto the visual grid (8) of their garden which the user can manipulate the positioning of. The user can continue to add (23) plants to the visual grid and manipulate as desired until there is no more available space. Collision detection software code prevents the plant blocks from intruding into the spacing requirements of each other. As plants are added, the filtered available plant list (20) is further amended to suggest companion plants with mutual benefits as well as warnings against plants with negative companion effects.

As the user adds plants to the virtual seedsheet, the price of the seedsheet is calculated (1) based on garden size and types and amounts of seeds included. Additionally the comparative costs of average retail produce may be calculated (2) to provide the user with an estimate of savings. Based on the germination percentage of each selected plant type as well as mutual compatibility with the other plants selected, an estimated garden-wide germination percentage may be calculated (3). The days-to-maturity/DTM for each selected plant may be calculated and graphed (5) to aid the users' design, especially vital when designing a seedsheet with a particular meal in mind. Lastly an instructional video (13) and narrative (14) may provide the user with any needed assistance in the creation of their seedsheet. All of the above inputs and constraints described relating to seed selection, spacing requirements, etc., are referred to as the plant algorithm.

A sheetsheet may include any number of rows and columns of grow holes, according to the size constraints the user may have for available ground on which to plant the sheetsheet. Similarly, the seedsheet may contain different seeds in different grow holes, optimized according to compatibility between the different plants, and other constraints.

Once the desired plant arrangement is finalized the user may purchase the seedsheet, preferably online, with the seedsheet produced by the vendor. The user's designed digital sheet is then transcribed to a weed barrier, or weed-blocking fabric layer. In the preferred embodiment, the weed fabric layer is a UV resistant, hydrophilic treated, weed barrier landscape fabric (15), with other suitable materials also usable. Per the users' digital design, or the manufacturer's design, grow holes (16) which are circular holes approximately five centimeters in diameter, are cut from the weed barrier fabric corresponding to each individual pod's location. In the preferred embodiment, each pod is circular in shape, and composed of layers of water-soluble film that are affixed together in a manner in which cavities are formed. The seed cavity (32), which is formed between the secondary (28) and tertiary (31) layers of water-soluble material, contains the designated plant seeds (33), and its centralized location ensures plant germination in the middle of each pod, thereby removing the potential for seeds to shift beneath the weed barrier and not germinate.

Between the secondary (28) and primary (27) layers of water-soluble film is the growing medium cavity, or uppermost cavity (29). Uppermost cavity (29) containing soil, peet, coir, compost or otherwise similar growing medium, is filled to a depth of approximately 1.5 cm with growing medium. The seed cavity (32) is formed between the secondary layer (28) and tertiary layer (31), and is expansive enough to hold a plurality of seeds (33), and to ensure germination each pod includes a multitude of selected seeds, ranging between 2 and 15 depending upon plant type. The physical properties of the water-soluble material layers allows each pod to completely and securely contain the growing medium (30) and plant seeds (33), and retain its shape and protective attributes until coming into contact with water. Upon watering, the soluble material rapidly dissolves, thereby allowing moisture to propagate through the growing medium and seeds, thus activating the germination process of the seed.

Figure 7:
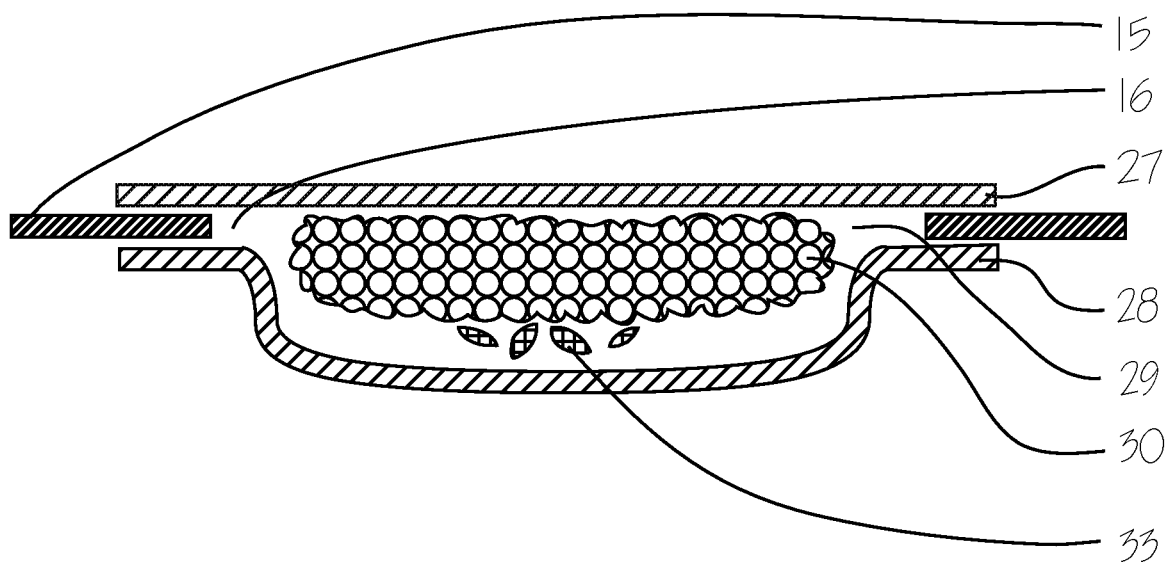
FIG. 7 shows alternate embodiment of a seedsheet with a soil and seed combination cavity
Figure 8:
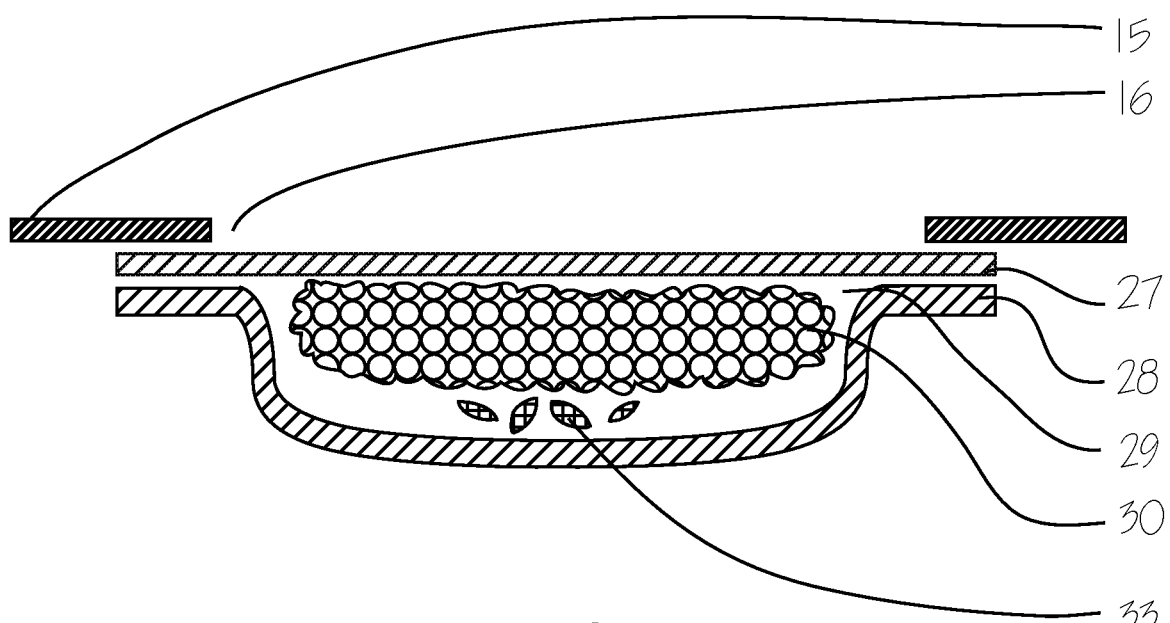
FIG. 8 shows alternate embodiment of a seedsheet with a soil and seed combination cavity

An alternate embodiment of the system uses a soil and seed combination cavity, and omits the tertiary layer (31), as shown in FIGS. 7 and 8. In FIG. 7, a dissolvable primary layer (27) is applied to the weed fabric layer's (15) upper surface, thereby covering each grow hole (16). The dissolvable layer is formed by a 6 cm circle of adhesive Polyvinyl Alcohol (PVA) fabric, but other suitable materials and dimensions may also be used. The bottom-side of each grow hole (16) is covered with approximately 1.25 cm of growing medium (30). The plant seed (33) is then placed beneath the soilless medium. A dissolvable secondary layer (28) is adhered to the weed fabric layer's lower surface, with the preferred embodiment using a 9 cm circle of PVA fabric, but other suitable materials and dimensions may also be used. FIG. 8 shows another embodiment of a soil and seed combination cavity, in which the upper surface of primary layer (27) is affixed to the lower surface of weed fabric layer (15). This is similar to the configuration of the preferred embodiment, but with a combination seed and soil cavity.

Figure 4:
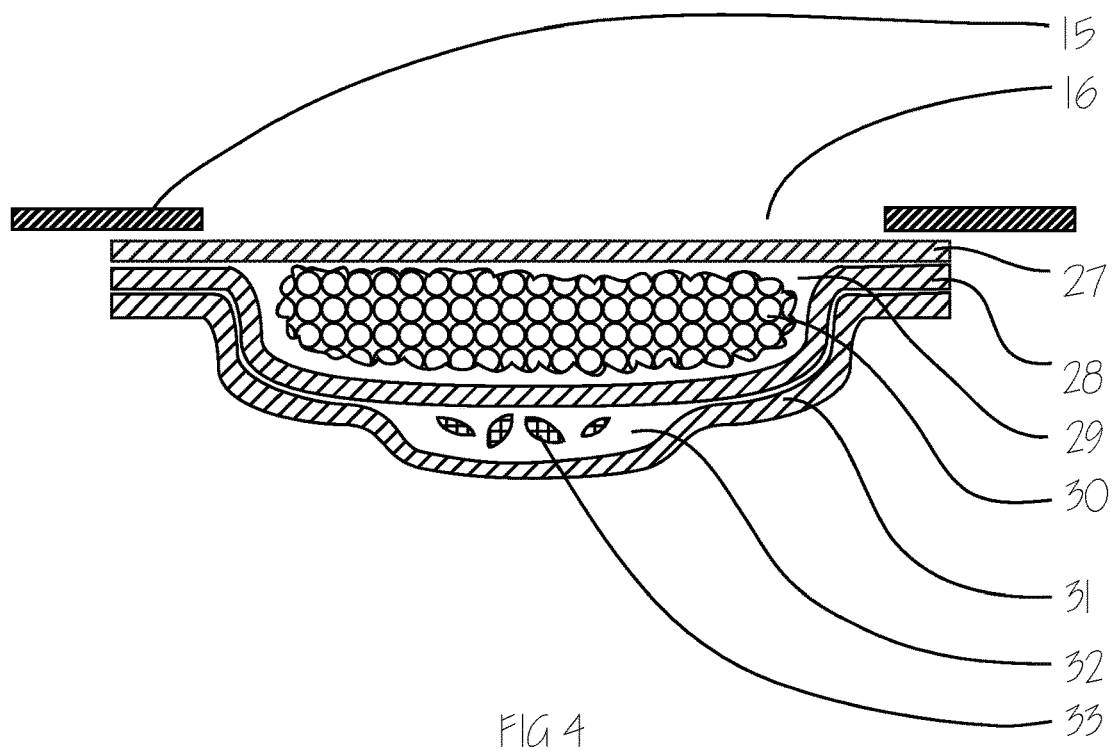
FIG. 4 shows a section view of a seedsheet Pod assembly
Figure 5:
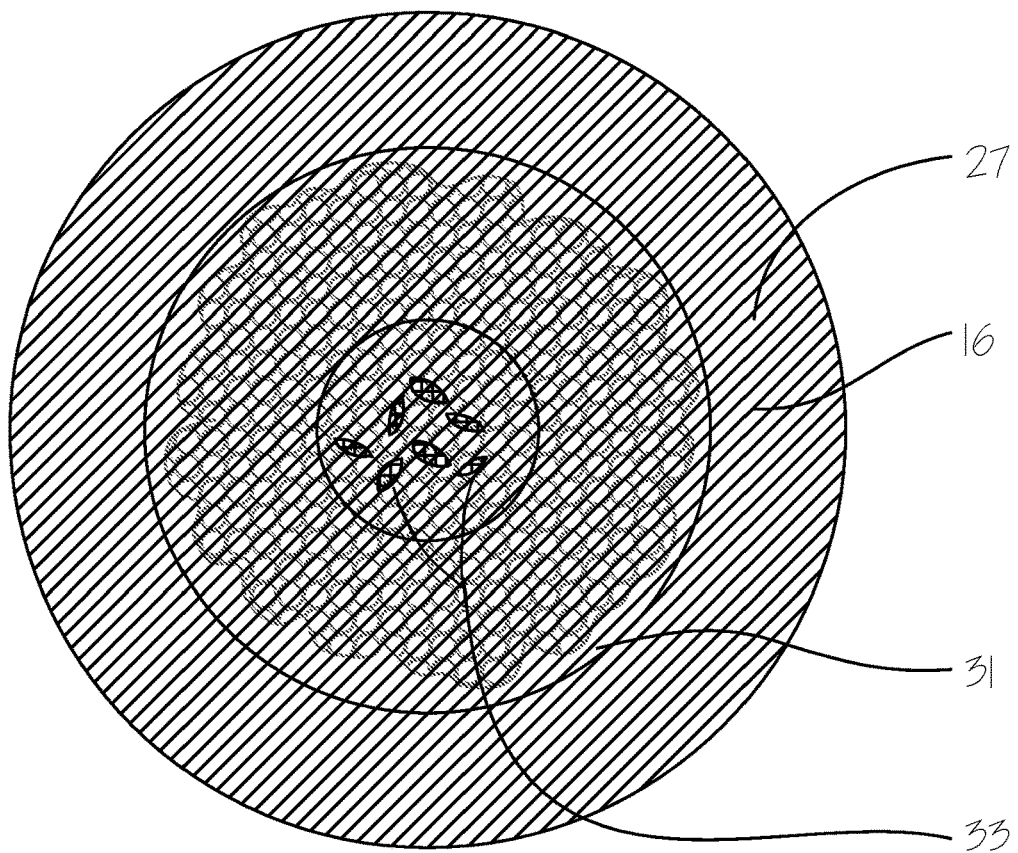
FIG. 5 shows an underside plan-view of a seedsheet Pod

The assembled seedsheet is simply unfurled atop an existing garden or tilled/prepared ground, and may be secured with stakes, and then watered. Once water is added, manually or by weather, the pods (FIG. 4) rapidly dissolve leaving the desired seed an opening to grow upward, and space below for its roots to develop. The seedsheet aids in the germination process by stabilizing the soil against extreme weather events, warms the soil through sunlight absorption to optimal germination temperatures (55-75° F.), and slowly filters high-water events through gradual permeation.

Each pod in the preferred embodiment is constructed from three layers of water-soluble film, and (heat) sealed together through a manufacturing process resulting in two separate, centrally located cavities. The uppermost cavity (29) contains the growing medium (30), and the bottom-most cavity (32) contains the plant seeds (33). The manufacturing process begins by placing the tertiary layer (32) upon a vacuum platen which uses forced air suction to depress the material downwards into a reservoir chamber. Seeds are then placed atop the tertiary layer into the formed depressed cavity. The secondary layer (28) is then laid over the top of the tertiary layer and cavity and sealed together, thereby resulting in an enclosed cavity in which the seeds securely reside. The sealed tertiary and secondary layers, which now include a formed seed cavity (32), are then placed atop a different vacuum platen which depresses the two layers and cavity downwards into a new reservoir chamber. Growing medium (30) is then poured into the formed cavity until becoming level with the top of the cavity, resulting in approximately 1.25 cm of soil depth. Lastly the primary layer (27) of water-soluble film is placed over the top of the secondary layer and growing medium and sealed.

Pods are affixed to the weed barrier material (15), and centrally aligned with the growhole cutout openings (16). The cutout openings, or seed holes, are preferably circular in diameter. In the current embodiment the upper flap of the pod, seen in FIG. 4 (27), is affixed to the weed barrier material through an ultra-sonic weld, however this process includes but is not limited to affixing through adhesives, embossing, sewing, crimping, stakes, and staples. The various layers of the pod are affixed to each other, as well as the weed barrier layer, along the perimeter of the grow hole. In the preferred embodiment, the pod and the grow hole are circular, though other shapes (such as rectangular) could be used, with sealing along the perimeter of the alternate shape. The completed seedsheet is placed seed-side-down atop prepared soil, secured with stakes, and watered, to begin seed germination and growth.

Figure 6:
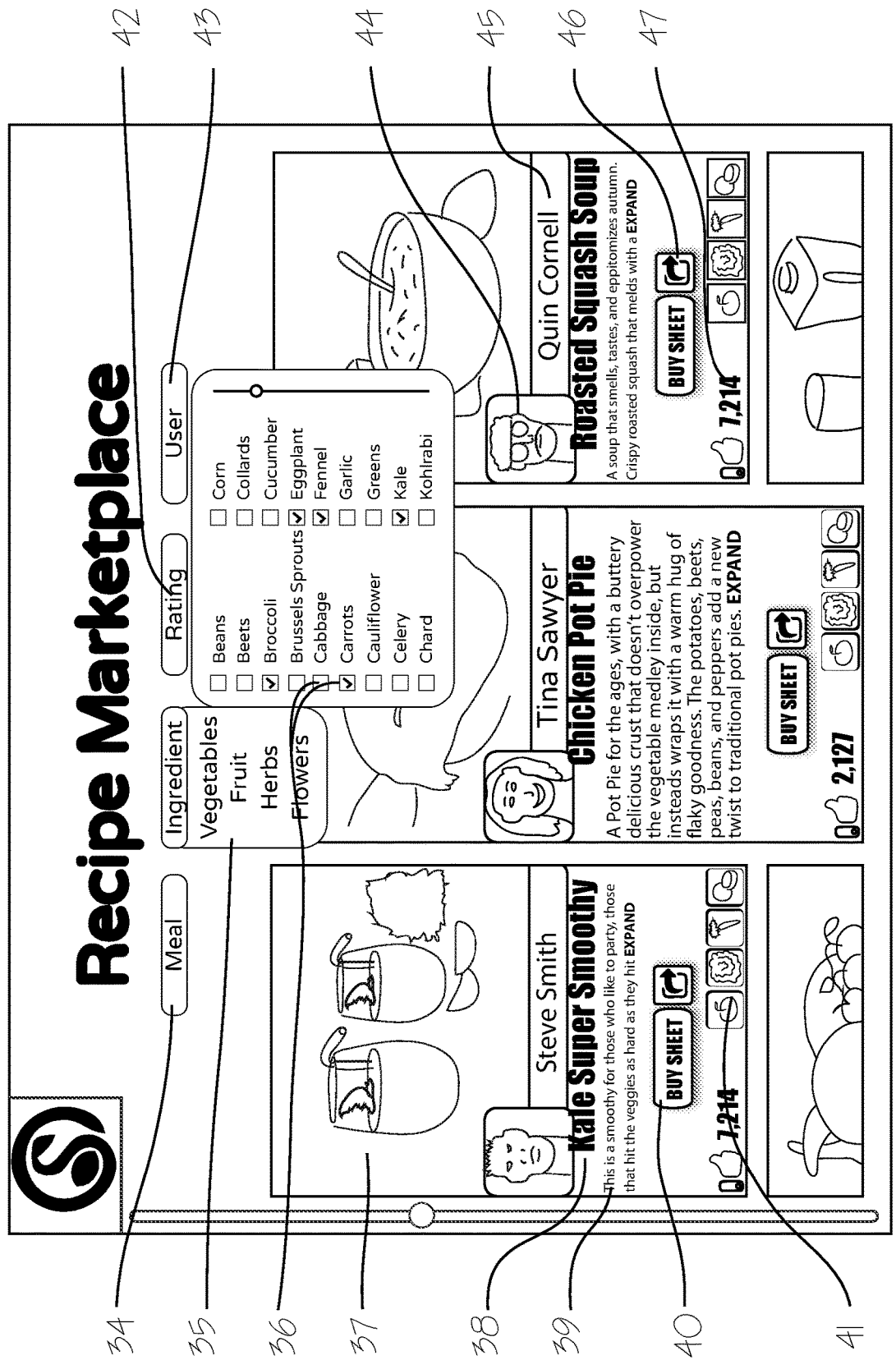
FIG. 6 shows an interface for relating recipes to garden planning

As seen in FIG. 6, the software may further include the ability to search for recipes (37) that include some or all of the ingredients contained within each user's specific seedsheet. This seedsheet recipe database (FIG. 6) is preferably a user-generated platform and marketplace that provides the ability for a user to create a profile (44, 45), input a recipe (38), description of recipe (39) and ingredient list that is linked to each type of included plant ingredient (41). The user then can generate a seedsheet containing some or all of the plants necessary for that specific recipe. When another user chooses to purchase a seedsheet for a specific recipe (40) the user who generated that recipe may receive a royalty amount. The database can be navigated by filtering recipes by type of meal (34), the plants contained within a user's seedsheet, or can be manually filtered by ingredients the user has on hand (35, 36), by rating (42, 47), and by user type (43). Thus, the seedsheet recipe database may be used in one or more ways. The first method allows a user to search for recipes using ingredients from the plants in their seedsheet. A second method is to generate a seedsheet using the ingredients required in one or more specific recipes. Other icons are shown at 6, 7, and 46.

The seedsheet Recipe Database may provide users the ability to monetize their recipes by integrating their ingredients into a purchasable seedsheet. Using a royalty payment structure and discounted store credits, users are thereby incentivized to share their recipes across their own social networks to increase their recipes rating. The integration of the Recipe Database within the entire platform serves to further demonstrate the complete garden-to-table cycle of this system. The software provides the user the ability to design and layout their garden with the seedsheet creator, simply plant their garden using the seedsheet, and find recipes directly pertaining to the plants available.

Although the present system has been described with respect to one or more embodiments, it will be understood that other embodiments of the present system may be made without departing from the spirit and scope of the present system. Hence, the present system is deemed limited only by claims and the reasonable interpretation thereof.

What is claimed:

1. A method for selecting and growing plants, comprising:
    creating a seedsheet with at least one grow hole in a weed barrier layer;
    affixing a dissolvable primary layer to said weed barrier layer's lower surface at said grow hole's perimeter;
    affixing a dissolvable secondary layer to said primary layer's lower surface at said grow hole's perimeter;
    forming an enclosed soil cavity between said secondary layer and said primary layer at said grow hole and placing soil in said cavity;
    affixing a dissolvable tertiary layer to said secondary layer's lower surface at said grow hole's perimeter;
    forming an enclosed seed cavity between said tertiary layer and said secondary layer at said grow hole and placing seeds in said cavity, with said seeds included only in said enclosed seed cavity; and
    placing said seedsheet on prepared soil to begin plant germination and growth.

2. The method of claim 1, in which said seedsheet includes rows and columns of multiple said grow holes.

3. The method of claim 1, in which a plant algorithm is used to select said seeds and said grow holes' position on said seedsheet.

4. The method of claim 2, in which seeds for one type of plant are placed in at least one grow hole, and seeds for a different type of plant are placed in at least one other grow hole.

5. A seedsheet system for selecting and growing plants, comprising:
    a weed barrier layer containing at least one grow hole;
    a dissolvable primary layer which spans said grow hole and is affixed to said weed barrier layer's lower surface at said grow hole's perimeter;
    a dissolvable secondary layer affixed at its edge to said primary layer's lower surface and spanning said grow hole;
    an enclosed soil cavity formed between said secondary layer and said primary layer at said grow hole, in which growing medium is included only in said enclosed soil cavity;
    a dissolvable tertiary layer affixed at its edge to said secondary layer's lower surface and spanning said grow hole; and
    an enclosed seed cavity formed between said tertiary layer and said secondary layer at said grow hole, in which seeds are included only in said enclosed seed cavity.

6. A seedsheet system for selecting and growing plants, comprising: a weed barrier layer containing at least one grow hole;
    a dissolvable primary layer which spans said grow hole and is affixed to said weed barrier layer's lower surface at said grow hole's perimeter; a dissolvable secondary layer affixed at its edge to said primary layer's lower surface and spanning said grow hole;
    an enclosed soil cavity formed between said secondary layer and said primary layer at said grow hole;
    a dissolvable tertiary layer affixed at its edge to said secondary layer's lower surface and spanning said grow hole; and
    an enclosed seed cavity formed between said tertiary layer and said secondary layer at said grow hole, in which seeds are included only in said enclosed seed cavity.

7. The system of claim 6, in which growing medium is included in said enclosed soil cavity.

8. The system of claim 6, in which said growing medium has a depth of approximately 1.25 cm.

9. The system of claim 6, in which a plant algorithm is used to select said seeds and said grow holes' position on said seedsheet.

10. The system of claim 6, in which said seedsheet system includes multiple grows holes arranged in columns and rows.

11. The system of claim 6, in which seeds for one type of plant are placed in at least one grow hole, and seeds for a different type of plant are placed in at least one other grow hole.

12. The system of claim 6, in which said dissolvable primary, secondary, and tertiary layers are composed of polyvinyl alcohol fabric.

\* \* \* \* \*